United States Patent
Townsend et al.

(10) Patent No.: US 7,478,108 B2
(45) Date of Patent: Jan. 13, 2009

(54) DATA COLLECTION USING SENSING UNITS AND SEPARATE CONTROL UNITS WITH ALL POWER DERIVED FROM THE CONTROL UNITS

(75) Inventors: Christopher P. Townsend, Shelborne, VT (US); Steven W Arms, Williston, VT (US)

(73) Assignee: Micro Strain, Inc., Williston, VT (US)

( * ) Notice: Subject to any disclaimer, the term of this patent is extended or adjusted under 35 U.S.C. 154(b) by 27 days.

(21) Appl. No.: 09/731,066

(22) Filed: Dec. 6, 2000

(65) Prior Publication Data

US 2002/0024450 A1      Feb. 28, 2002

Related U.S. Application Data

(60) Provisional application No. 60/169,364, filed on Dec. 6, 1999.

(51) Int. Cl.
*G06F 17/00* (2006.01)
*G08B 23/00* (2006.01)

(52) U.S. Cl. .................................. 707/104.1; 340/500
(58) Field of Classification Search ............. 707/104.1; 705/2, 3; 340/539, 540; 320/138; 188/378; 607/32, 33, 34
See application file for complete search history.

(56) References Cited

U.S. PATENT DOCUMENTS

| | | | | |
|---|---|---|---|---|
| 4,041,955 A | 8/1977 | Kelly et al. | ................. | 653/464 |
| 4,071,032 A | 1/1978 | Schulman | ................... | 128/419 |
| 4,096,866 A * | 6/1978 | Fischell | ....................... | 607/34 |
| 4,142,533 A | 3/1979 | Browniee et al. | .......... | 128/419 |
| 4,532,930 A | 8/1985 | Crosby et al. | ............... | 128/419 |
| 4,612,934 A | 9/1986 | Borkan | ...................... | 128/421 |
| 4,741,339 A | 5/1988 | Harrison et al. | ............. | 789/874 |
| 5,005,678 A * | 4/1991 | Julien et al. | ................. | 188/378 |
| 5,193,539 A | 3/1993 | Schulman et al. | ........... | 128/419 |
| 5,300,875 A * | 4/1994 | Tuttle | ......................... | 320/138 |
| 5,405,367 A | 4/1995 | Schulman et al. | ............ | 607/61 |
| 5,476,488 A | 12/1995 | Morgan et al. | ................ | 607/30 |
| 5,562,714 A | 10/1996 | Grevious | ..................... | 607/32 |
| 5,565,862 A * | 10/1996 | Hubbard et al. | ....... | 340/870.11 |
| 5,608,171 A | 3/1997 | Hunter et al. | ............ | 73/861.63 |
| 5,619,417 A | 4/1997 | Kendall | ..................... | 364/483 |
| 5,735,887 A | 4/1998 | Barreras, Sr. et al. | ......... | 607/60 |
| 5,978,738 A | 11/1999 | Brown | ........................... | 702/3 |

(Continued)

*Primary Examiner*—Uyen T. Le
(74) *Attorney, Agent, or Firm*—James Marc Leas

(57) ABSTRACT

A data collection apparatus includes a sensing unit for attaching to a structure or live subject for sensing a parameter of the structure or live subject. The sensing unit includes a sensor, a data storage device, and a transmitting device. The data storage device is for storing data from the sensor. The apparatus also includes a control unit that is separable from the sensing unit. The control unit includes a data receiving device and a second data storage device different from said first storage device. The data receiving device is to receive data transmitted from the data sensing unit. The second data storage device is for storing the data received from the sensing unit. The apparatus also includes a triggering device for modifying the storing of data being stored to the first data storage device or for initiating transmission of data from the sensing unit to the control unit. The triggering device is controlled by a real time change in information about the structure or live subject.

73 Claims, 5 Drawing Sheets

U.S. PATENT DOCUMENTS

| | | | |
|---|---|---|---|
| 5,978,972 A | 11/1999 | Stewart et al. | 2/422 |
| 5,987,352 A * | 11/1999 | Klein et al. | 600/509 |
| 6,067,474 A | 5/2000 | Schulman et al. | 607/57 |
| 6,127,799 A | 10/2000 | Krishnan | 320/104 |
| 6,133,830 A * | 10/2000 | D'Angelo et al. | 340/539 |
| 6,164,284 A * | 12/2000 | Schulman et al. | 128/899 |
| 6,208,247 B1 * | 3/2001 | Agre et al. | 340/539 |
| 6,351,670 B1 * | 2/2002 | Kroll | 607/5 |
| 6,624,750 B1 * | 9/2003 | Marman et al. | 340/506 |

\* cited by examiner

FIGURE 5

| PARAMETER/ SENSOR + TYPE | Typical Sensor Power Consumption | Typical gain range requirement | StrainLink-DC Compatible | StrainLink-AC Compatible |
|---|---|---|---|---|
| TEMPERATURE Thermocouple | 0 | 128 | YES | NO |
| TEMPERATURE Thermistor | 5 mW | 32-64 | YES | NO |
| TEMPERATURE RTD | 5 mW | 32-64 | YES | NO |
| STRAIN Foil Strain Gauge Bridge | 10 mW-30mW | 128 Minimum | YES | NO |
| STRAIN Semiconductor Strain Gauge Bridge | 0.5 mW- 5 mW | 32-128 | YES | NO |
| STRAIN Capacitive Strain Gauge | <5 mW | 128 | NO | YES |
| FORCE Force Sensing Resistor | <1 mW | 1 | YES | NO |
| FORCE Foil Strain Gauge | 10mW - 30mW | 128 Minimum | YES | NO |
| PRESSURE MEMS Piezoresistive Pressure Sensor | 0.5 mW- 5 mW | 32-128 | YES | NO |
| ACCELERATION Piezoelectric Accelerometer | 0 | 64 - 128 | YES | NO |
| ACCELERATION MEMS Piezoresistive Accelerometer | 0.5 mW- 5 mW | 32-128 | YES | NO |
| MAGNETIC FIELD Magnetoresistance | 1mW-25 mW | 32-128 | YES | NO |
| MAGNETIC FIELD Hall Effect | 10 mW - 25 mW | 16-64 | YES | NO |
| ROTARY Potentiometer | <1 mW | 1 | YES | NO |
| HUMIDITY Capacitive | <10mW | 64-128 | NO | YES |
| CRACK PROPAGATION Resistive | <10mW | 16-64 | YES | NO |
| DISPLACEMENT DVRT /LVDT | 10mW-25mW | 128 | NO | YES |
| DISPLACEMENT Potentiometer | <1mW | 1 | YES | NO |
| DISPLACEMENT Non-Contact Inductive | 10 mW-25 mW | 128 | NO | YES |
| LIGHT INTENSITY Silicon Photodetector | <1mW | 64-128 | YES | NO |
| VELOCITY- DVRT | 0 mW | 64-128 | YES | NO |

DATA COLLECTION USING SENSING UNITS AND SEPARATE CONTROL UNITS WITH ALL POWER DERIVED FROM THE CONTROL UNITS

This application claims priority of U.S. Provisional Patent Application 60/169,364, filed Dec. 6, 1999.

FIELD OF THE INVENTION

This invention generally relates to collecting and transmitting data. More particularly, it relates to a device for sensing, storing and transmitting data. Even more particularly, it relates to a device that can be attached to a structure or live subject for providing data about the structure or live subject.

BACKGROUND OF THE INVENTION

Art, photography, and scientific literature record long standing interest in how humans or animals run, and details of what happens in a collision. Various systems for sensing, collecting, storing, and communicating data about moving systems and remote locations have been described in the literature.

For example, in virtual reality systems the motion of the head and other extremities is continuously monitored to provide feedback to the computer to enable updating of images, as mentioned in U.S. Pat. No. 5,978,972 to Stewart et al (the "'972 patent"). The '972 patent also notes that systems have been developed for military applications to monitor the orientation of a pilot's head to assist in targeting. For these applications the helmets must remain hardwired to support infrastructure.

One system for measuring and recording acceleration of a person's head in a sports helmet that does not require hard wiring to extensive support infrastructure is described in the '972 patent. The system provides accelerometers in the helmet for sensing impacts. The accelerometers communicate with memory for recording in real time data from the accelerometers. The memory can be in the helmet itself or data can be transmitted from the helmet to a nearby receiver for storage there, for example, on a computer hard drive. Either way, the data collected from the accelerometers can be analyzed to detect the precise motions of the head which precede a severe head injury.

A weather station described in U.S. Pat. No. 5,978,738 to Brown, describes a scheme for collecting weather data from a remote location. The station has two separable sections. A sensor section measures and records weather related information, such as local temperature, pressure, humidity, ambient light, and ambient static charge, for periodic transmission to a receiver section. The receiver section can also communicate with global weather reporting systems.

Other systems, such as the black box on an aircraft, store data from sensors on a recording device having limited storage capacity. Stored data is periodically overwritten and only the data for a specified time period leading up to an event, such as a crash, is available after the event. The black box must then be found so the data stored can be retrieved.

Other systems transmit external data in real time into a live subject, for example, to stimulate human organs, such as heart or ear, as described in U.S. Pat. No. 4,532,930. Others transmit energy under the skin, for example, for recharging an implanted battery, as described in U.S. Pat. No. 6,067,474 to Schulman et al. These systems do not generally sense, collect, and store data though.

All the systems that sense and collect data, store the data, and then communicate the data have inefficiencies either in the data acquisition or in the transmission of the data. Thus, a better system for acquiring and transmitting data is needed, and this solution is provided by the following invention.

SUMMARY OF THE INVENTION

It is therefore an object of the present invention to provide a scheme for collecting data that avoids collecting large amounts of unwanted data and that collects desired data to provide more efficient data collection;

It is a further object of the present invention to provide a data collection device that can be triggered in real time;

It is a further object of the present invention to provide a data collection device that can be triggered by an event sensed by the device;

It is a further object of the present invention to provide a data collection device that can be remotely triggered by a user;

It is a feature of the present invention that remote triggering of the data collection device provides transmission of stored data from a time before an event occurred;

It is a further feature of the present invention that the data collection device has a sensing unit and a control unit, and the sensing unit has a receiver to receive a trigger signal from the control unit; and It is an advantage of the present invention that the data collection device can provide real time data triggered by an event or by a user in response to a change in information about the structure or live subject.

These and other objects, features, and advantages of the invention are accomplished by a data collection apparatus that includes a sensing unit for attaching to a structure or live subject for sensing a parameter of the structure or live subject. The sensing unit includes a sensor, a data storage device, and a transmitting device. The data storage device is for storing data from the sensor. The apparatus also includes a control unit that is separable from the sensing unit. The control unit includes a data receiving device and a second data storage device different from said first storage device. The data receiving device is to receive data transmitted from the data sensing unit. The second data storage device is for storing the data received from the sensing unit. The apparatus also includes a triggering device for modifying the storing of data being stored to the first data storage device or for initiating transmission of data from the sensing unit to the control unit. The triggering device is controlled by a real time change in information about the structure or live subject.

BRIEF DESCRIPTION OF THE DRAWINGS

The foregoing and other objects, features, and advantages of the invention will be apparent from the following detailed description of the invention, as illustrated in the accompanying drawings, in which:

FIG. 5 is a table illustrating the variety of sensors that can be used with the present invention;

DETAILED DESCRIPTION OF THE INVENTION

Figure 1:
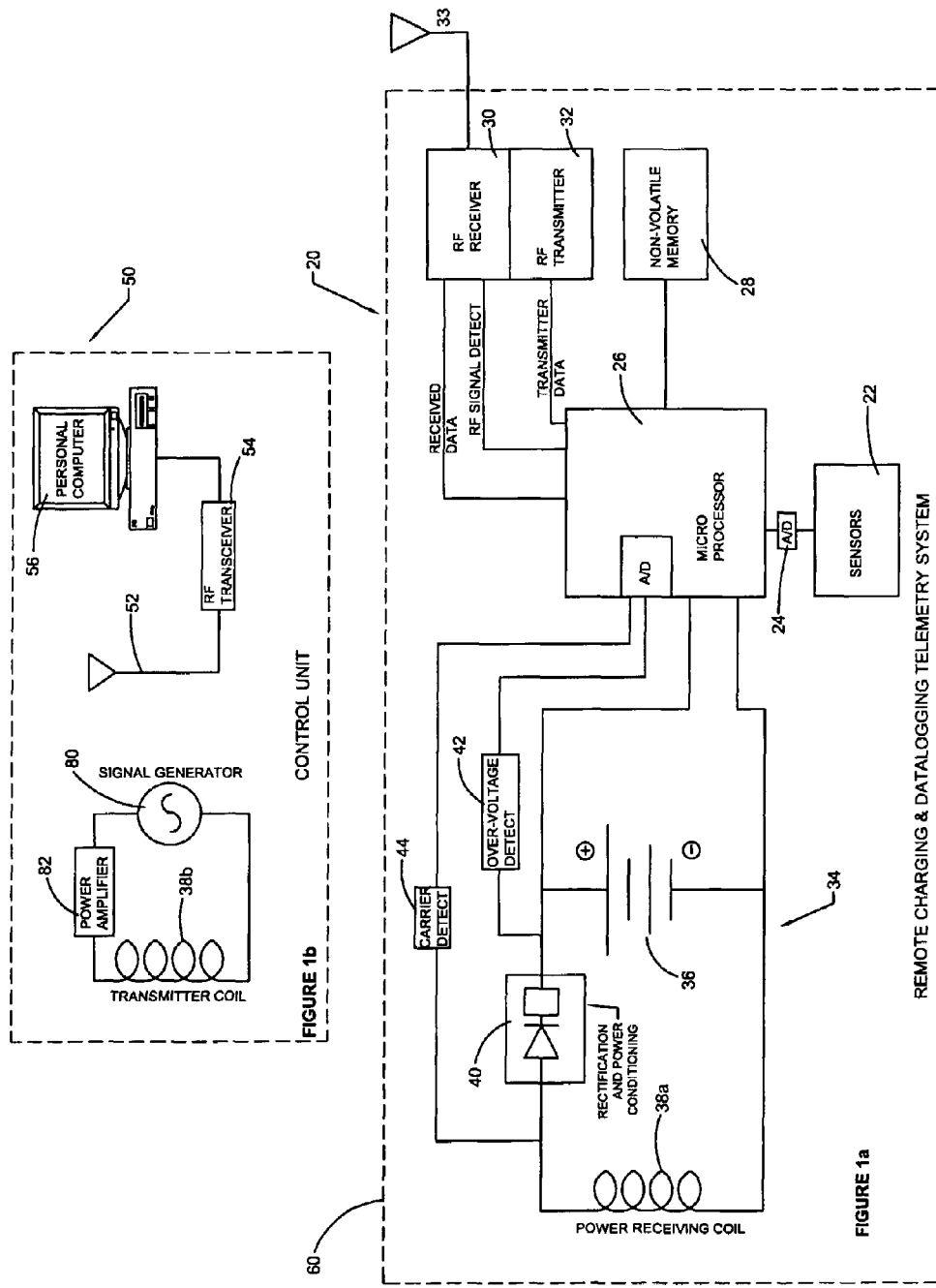
FIG. 1a is a block diagram of a sensing unit of the present invention.
FIG. 1b is a block diagram of a control unit of the present invention.

The present inventors recognized that substantial efficiency in collecting, storing, and transmitting data could be provided. They recognized that data from a moving or remote structure or live subject may be provided by mounting a sensing unit in or on the structure or subject of interest. In one embodiment, the sensing unit has both a sensor and a data storage device for storing data from the sensor. The inventors further recognized that providing a scheme in which the data storage is controlled by a real time trigger solves a problem with previously existing systems.

In one embodiment of the invention, accelerometers, data storage, and a triggering scheme are mounted in a wearable device such as a sports helmet. The triggering scheme can be data collected by the accelerometers that exceeds a predetermined threshold. The above-threshold data may be caused by an event, such as a collision. If the high acceleration produced by a collision and measured by the accelerometers exceeds the threshold this data triggers a change in data handling. For example, data stored during a specified time period before the triggering event may be retained and data may continue to be collected and retained during and after the event. Data collected from times before this specified time period may not be retained. The system thus automatically distinguishes wanted and unwanted data. The triggering can also provide for transmission of this data to a control unit.

Triggering can also be provided by a change in other information about the structure or live subject being monitored. In addition to information sensed by the sensors themselves, a change in information otherwise observed about the structure or live subject by the analyst or by other sensors can provide the trigger. In addition to a change in information being an increase in activity or another parameter, a change in information can also be detection of no change in activity for an extended period of time, for example, indicating the death of the live subject, or indicating potential injury from inactivity or repetitive stress.

The triggering scheme can be a signal transmitted to a receiver that is mounted in the helmet. The signal may be transmitted at any time by an analyst at the control unit based on an observation of a change in some information about the structure or live subject. The signal may initiate data storage or it may initiate data transmission. With either self-triggering or external triggering, collection and storage of massive amounts of unwanted data is avoided, while the specific data wanted is collected for transfer to the control unit.

Data collection system 20 includes sensor 22 connected to analog to digital (A/D) converter 24 connected to microprocessor 26. Sensor 22 can be an accelerometer, displacement sensor, strain gauge, pressure gauge, thermometer, heart rate, EKG, or EEG monitor, blood test data monitor, force gauge, humidity monitor, growth rate or ripeness monitor, light intensity gauge, radiation detector, chemical detector, corrosion detector, or toxic gas monitor. A/D converter 24 converts analog sense data to digital data that can be processed by microprocessor 26. A/D converter 24 can be of the successive approximation type, such as Texas Instruments TLC 2543; the Sigma Delta type, such as Analog Devices AD7714; or the on board microcontroller type, such as Microchip PIC16F8xx series or Motorola MC68HC11. A/D converter 24 can be integrated on one chip with microprocessor 26.

Microprocessor 26 can be located on a micro-controller which has other functions on board, such as A/D converter, memory, communications ports, and multiplexers. Microprocessor 26 can save a unique address for each sensor unit in memory 28 so that microprocessor 26 it can query, activate, or send timing information to each sensor individually or to all sensors at once. For example the Microchip PIC16F8xx series is a microcontroller that includes microprocessor, A/D converter, non-volatile flash memory, communications port, and SRAM. Microprocessor 26 reads A/D converter, manages the programming of non-volatile memory and sends sensor readings to the memory, communicates to the control unit, provides for error checking on received and transmitted data, stores scaling coefficients to convert A/D bit values into physical units, manages threshold triggering or external triggering. The program to run the microprocessor is stored in non-volatile memory. This memory may be on the microprocessor chip or on an external non-volatile memory chip. The operation of these programs can be changed by transmitting programming data to microprocessor 26 of sensor unit 20. Also connected to microprocessor 26 are memory 28, RF receiver 30, RF transmitter 32, and power supply 34.

Memory 28 can be non-volatile memory, such as flash memory, disk drive, or tape drive. Receiver 30 can use radio communications of the amplitude shift keyed, frequency shift keyed, or spread spectrum variety. For example, the RF Monolithics TR1000 transceiver provides RF communications in both directions in a very small package and consumes very little power. Transmitter 32 is included in this transceiver or it can be a separate component. Transmitter 32 can be a transformer coupled transmitter for short range data transfer, a radio transmitter, such as a narrow band transmitter or a cellular phone for long range transmission, or a hard wired transmitter, such as an RS232 twisted pair wires or a wired phone line, or ethernet connection for internet access. Antenna 33 is connected to receiver 30 and transmitter 32 for the RF transmitter type. It may be located outside housing 60 to allow RF communications unless housing 60 is made of a non-conductive material such as polymer, ceramic, or glass. In this case antenna 33 is a trace on a printed circuit board within housing 60. If housing 60 is formed of a conductive material, such as titanium, however, connection of antenna 33 must be through an insulated feed through.

Power supply 34 is assembled from different parts. For implanted use, power supply 34 includes battery 36, power receiving coil 38a, rectifier 40, over-voltage detect circuit 42 and carrier detect circuit 44. Battery 36 may be either a non-rechargeable type or a rechargeable type. Rechargeable batteries include nickel cadmium, nickel metal hydride, and lithium-ion. A fuel cell can also be used. Alternatively, power may be supplied by magnetic field coupling into a coil in the sensor unit from a coil in an adjacent unit. Carrier detect circuit 44 provides a signal that is proportional to the magnitude of the voltage coupled into power receiving coil 38a.

Threshold levels are including in the programming stored in non-volatile memory, and levels can be changed by communications from a remote device. The mode of triggering can be changed from triggering based on threshold to triggering from an external signal. These modes are also stored in non-volatile memory.

In operation, sensors 22 provide sense data to A/D converter 24 and then to microprocessor 26 for storage in non-volatile memory 28, as shown in FIG. 1a. Microprocessor 26 is programmed to recognize an event when data from sensor 22 that exceeds a threshold value. It is programmed by commands communicated from control unit 50. Programming can set the number of samples of sensed data collected per second, duration of data collection, and the number of sensors sampled at one time or in sequence. Data continues to be logged during the event and for a period of time after the event. In addition, a programmable portion of recent data stored in non-volatile memory 28 from before the event can be retained in memory so events leading up to the event can be analyzed as well. Thus, the amount of data retained in non-volatile memory can be programmed in advance. In addition to triggering this change from routine data logging, the event may also trigger transmission of data to control unit 50 which acts as a data reception system, as shown in FIG. 1b. Control unit 50 includes antenna 52, radio transceiver 54 and computer 56, such as a personal computer, hand held computer, or other microprocessor based device. Control unit 50 can also be connected to sense unit 20 through the internet. Thus, only desired data from time around the event is retained and transmitted to control unit 50. The event may be an acceleration higher than a preset value from a collision; displacement beyond a specified location providing excessive strain; elevated pressure, temperature, or heart rate; an out of spec level for EKG or EEG; blood test data that is out of normal range, etc. Alternatively, once the threshold level has been reached, data may be transmitted by transmitter 32 to control unit 50 in real time. In another alternative, a trigger signal can be transmitted from control unit 50 to receiver 30 which directs collection, storage, or transmission of data from sensor 24. For example, the received trigger signal can start data collection and storage or it can start transmission of stored data, real time data, or a combination of stored and real time data.

Data collection system 20 can be attached to a natural structure, such as an embankment, to soil to detect moisture, to an architectural structure, such as a building or bridge that is relatively difficult to access to detect inclination, subsidence, strain, or vibration, to a vehicle, such as an aircraft, or to a live subject, such as a person, animal, or plant. It can be attached to a hoof, implanted, or worn externally, such as in a helmet or belt. Data collection system 20 is very small in size and does not interfere with normal movement. The live subject can therefore be completely mobile, and is free to move as if data collection system 20 were not there at all.

Data collection system 20 is particularly suitable as an implantable device within the body of a human, animal, or plant for measuring internal parameters, such as temperature, blood flow or blood pressure levels, blood electrolyte and chemical levels, etc.

Power can be transmitted through the skin to implanted power supply 34. Power receiving coil 38 receives the AC transmission which is converted to DC in rectifying circuit 40 to recharge implanted battery 36. Data collection system 20 is enclosed in a hermetically sealed container 60 which protects the electronics from the corrosive effects of body fluids. The present inventors found that a metal case fabricated of titanium will permit sufficient radiated power to penetrate to fully charge battery 36. The case can also be fabricated of a ceramic material, such as Dow Corning Macor, which is machinable, and can be used to produce hermetic packages. For metal housings, receiving coil 38 can be connected to hermetically sealed electronics via a hermetic feed through and receiving coil 38 can be encapsulated in bio-compatable epoxy. This arrangement increases the efficiency of reception of power from control unit 50. Sensor 22 may be any sensing device, as described herein above, such as a sensor to detect implant micro-motion, internal pressure, torque, and loading.

Data collected by sensor 22 and stored in memory 28 is retained for transmission to control unit 50 upon receipt of a trigger signal. The trigger signal may be transmitted from control unit 50 and received by receiver 30. Alternatively it may be provided by the sensor data itself, as described herein above. A preset limit is programed in microprocessor 26, and when data exceeds that limit, data is stored, retained, or transmitted.

The system is particularly attractive for implantation since power required for storing data in memory 28 is two orders of magnitude less than required for real time transmission. Similarly, if data is only transmitted when the data reaches a predetermined threshold or when triggered by an external signal, substantially less power is used than is required for periodic transmission. Battery 36 is a lithium battery or another type of battery that provides long life and may be recharged many times. Recharging may be accomplished by placing the external control unit 50 within close proximity of sensor unit 20 so coils 38a and 38b are closely spaced to provide efficient magnetic coupling. Furthermore, these coils include ferrite cores to enhance coupling. Control unit 50 can program sensor unit 20 to reduce power consumption by shutting power to unused sensors and data acquisition electronics while maintaining capability of monitoring the state of charge of battery 36. Once sensor unit 20 is fully charged it transmits its state of charge to control unit 50 which displays that charging is complete on personal computer 56.

An alternative embodiment does not require an implanted battery but allows monitoring of implanted sensors, including measurements of motion, force, chemical composition, such as blood levels, and bioelectric parameters, such as EKG, EMG, and EEG. The development of improved implantable devices, such as orthopedic devices for replacement knees and hips, requires knowledge of their in vivo behavior. However, little is known about the actual loads borne by implanted devices in vivo. Direct load measurement would provide extremely valuable information, for the improvement of device designs, and for the rapid rehabilitation of individuals in which devices have been implanted. Multichannel telemetry systems, combined with strain gauges, can provide this information.

The lack of in vivo measurements may be limiting our ability to design the most effective orthopedic implants. Currently, the loads and moments are theoretically determined from mathematical models that are often based on idealizations of joint geometry, material properties, and muscle physiology. The use of cadaver specimens may not reflect an accurate model of the loads experienced in vivo.

In vivo data could be utilized in the design of new orthopedic implants or other health care products. Rehabilitation could be tailored to a specific patient, based on the knowledge provided by a smart implant. This would be more appropriate than prescribing the same rehabilitation protocol to every patient. Biofeedback could be provided to the patient to protect them from loads that could be damaging. Conceptually, data could be collected remotely without requiring an office visit by the patient. This could lower the cost of administering health care, and could allow for a patient to be more closely monitored.

If implantable telemetry systems are used in animal studies it would reduce the number of animals required to complete a chronic study. Currently, animals have to be sacrificed at predetermined time intervals to do chronic studies. The use of an implantable telemetry system would allow data to be collected over the length of the study on a single animal.

The present inventors developed an implantable telemetry system that can transmit data from multiple implanted sensors and is powered by inductively coupling energy from an external coil to an internal power reception coil. The design of this system and test results of load data that has been collected in vitro in a total knee implant will be described below.

The present system combines advanced, micropower, analog/digital integrated circuits with new, miniature, low power microprocessors to develop a versatile remotely powered, implantable sensor telemetry system.

Figure 2:
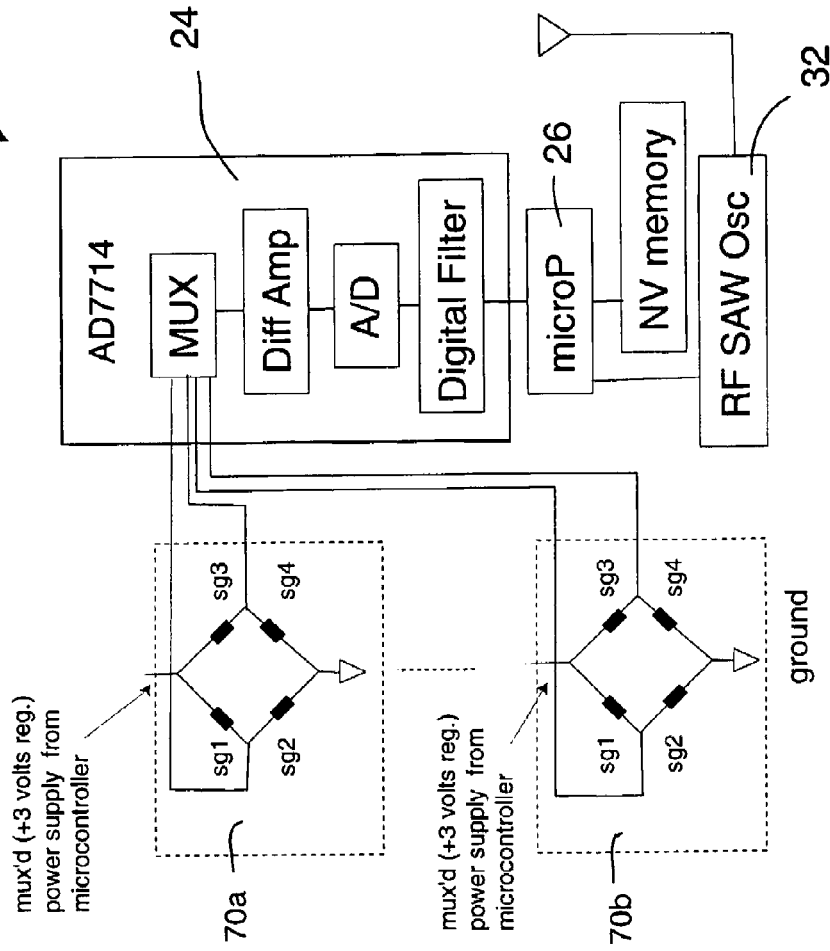
FIG. 2 is a block diagram of an alternate embodiment of a sensing unit of the present invention.

In the present embodiment, sensor unit 20' includes sensors 70a, 70b all connected to multiplexor 72 that is part of A/D chip 24 which can be Analog Devices AD7714 that provides signal conditioning as well as A/D conversion. The AD7714 features 3 true differential bridge inputs, 5 pseudo differential inputs, a maximum resolution of 22 bits, and software programmable gain of 1-128. Chip 24 also includes differential amplifier 72, A/D converter 74, and digital filter 76. Data output from A/D chip 24 is processed by microprocessor 26, which may be a PIC16C microcontroller, and is transmitted by transmitter 32, which can be an RF surface wave acoustic oscillator, as shown in FIG. 2.

The microprocessor (PIC16C, MicroChip Technologies, Chandler Ariz.) allows the AD7714 to be reprogrammed through the serial port of a personal computer (PC) before being implanted. Once programmed, the configuration is stored in nonvolatile, electrically erasable, programmable, read only memory (EEPROM), on the PIC16C. On power up, the PIC16C reads the EEPROM to configure the AD7714 for the appropriate channel specific gain, filtering, and sample rate parameters. If a receiver is included, it can be reprogrammed after implanting.

The microprocessor also performs pulse code modulation (PCM) of a surface acoustic wave (SAW) radio frequency (RF) oscillator (RF Monolithics, Dallas, Tex.). PCM modulation is advantageous because it is relatively less prone to interference compared to pulse width modulation (PWM) and pulse interval modulation (PIM). Furthermore, with PCM we are able to detect an error in RF transmission. This is accomplished by sending a checksum byte, which is the sum of the preceding data bytes. At the receiver, if the sum of the data bytes does not equal the checksum byte, then an error flag is generated at the PC based receiver.

Control unit 50 includes PCM receiver 54 which contains a matched RF SAW oscillator, a level converter to generate RS-232 signals from the PCM data stream, and PC based software to read, display and store the received data. It is noteworthy that the receiver is powered by a nine volt battery within a handheld enclosure, allowing the receiver to be wearable by the subject with the implanted sense unit.

The requirements for powering an implantable system are extremely demanding. The chemicals used in construction of the battery are often toxic and are not desirable in an implantable system, even if the batteries can be hermetically sealed within the implant. The operating life of the telemetry system will always be limited by the operating life of the battery. If a battery were to be used in an implantable application, then the single largest component of the telemetry system would be the battery. This would limit the use of the telemetry system to large implants.

To circumvent the use of batteries, remote powering is desirable. Magnetic near field coupling can be utilized to transfer power to the implanted coil. An external coil is driven with AC current generating an AC magnetic field. When the receive coil is placed in this field an AC voltage is generated on the receive coil. This voltage is then rectified and filtered to provide the DC power that is required to operate the telemetry system. Remote powering through an orthopedic implant presents a great challenge, as the efficiency of coupling is reduced greatly by the presence of the metal implant between the transmitting and receiving coil. Ideally, high frequencies (>125 kHz) would be utilized to increase the coupling efficiency. However, the combination of shielding and losses due to eddy currents presented by the implant preclude the use of higher frequencies. We found the most efficient frequency of operation with the titanium implant was 1.5 kHz.

Figure 3:
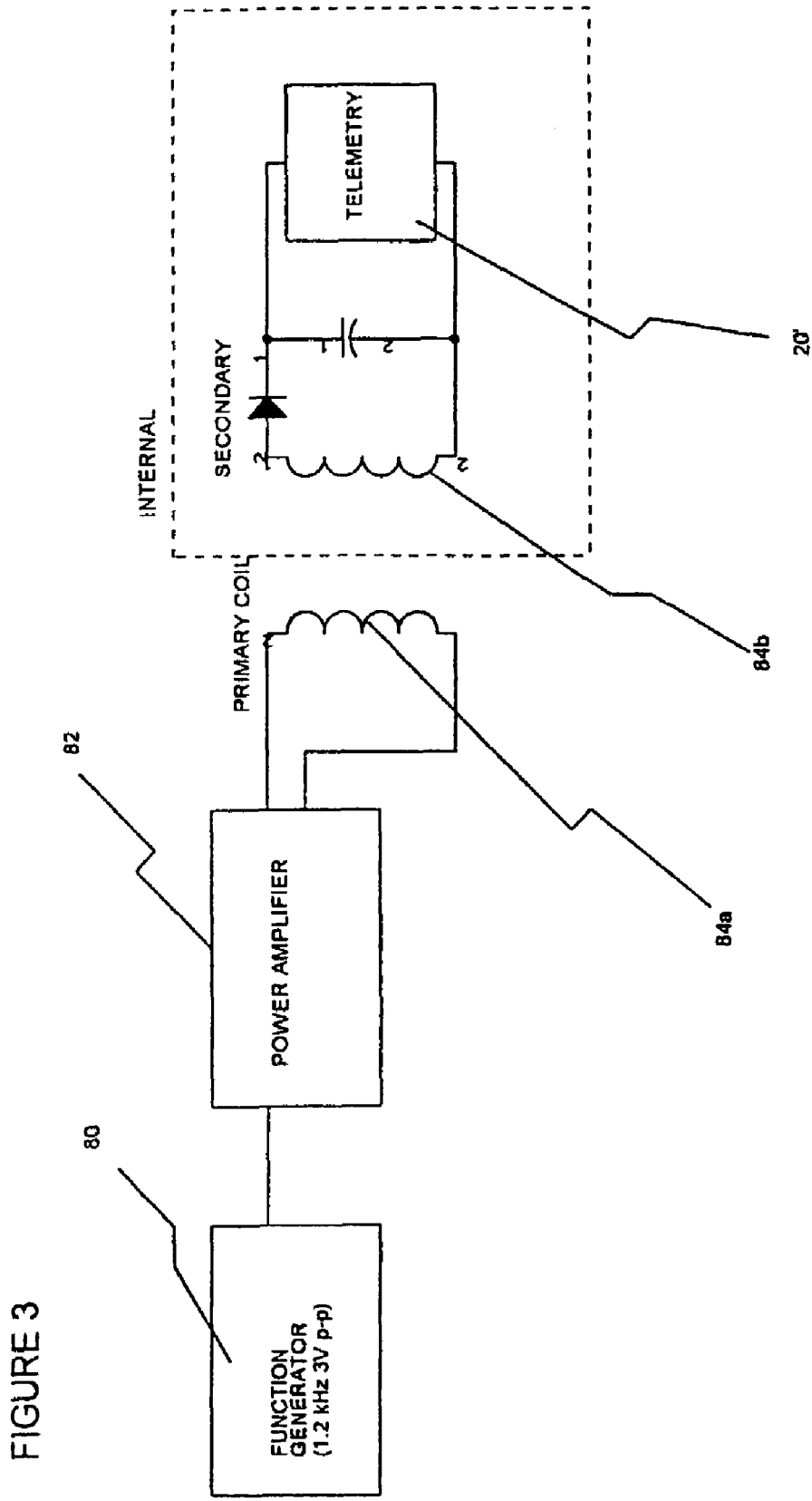
FIG. 3 is a block diagram of the powering scheme for the alternate embodiment in which power is transmitted to the sensing unit from the control unit.

As shown in FIG. 3, function generator 80 (B&K precision) provides a 3 V p-p AC signal at 1.6 kHz to 100 W audio power amplifier 82 (Samson, Inc.) which amplifies the signal and drives external (primary) coil 84a that is constructed of 35 turns of 16 gauge magnet wire. The impedance of external coil 84a was 10 Ohms at the 1.6 kHz drive frequency. The power amplifier delivered 1.0 Amp of current at 35 Volts to external coil 84a. External coil 84a is seven inches in diameter, which allows for the coil to be placed around a patient's leg. Internal (secondary) coil 84b consists of 2000 turns of magnet wire wound on a high permeability ferrite core. Approximately 40 milliwatts of power could be coupled into the internal coil 84b, which is more than adequate to power the telemetry system.

Figure 4:
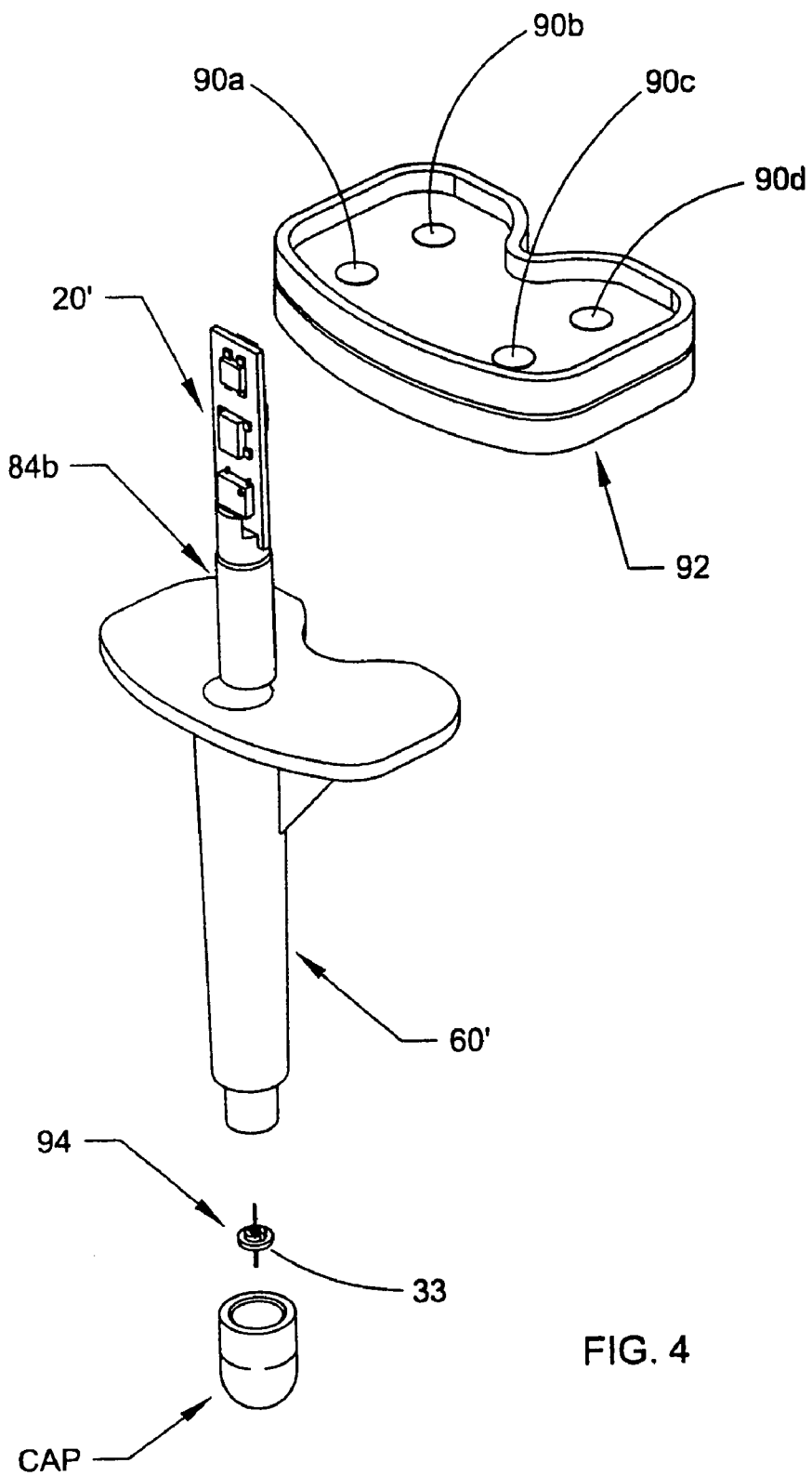
FIG. 4 is an exploded view of a replacement knee implant containing the alternate embodiment of the sensing unit hermetically sealed therein.

It is important that the addition of electronics to an implant not add additional size or risk to the patient. To minimize these risks it is a requirement that sense unit 20' and power reception coil 84b be hermetically sealed within the implant. An example of such an application is the use of such a telemetry system within a custom developed total knee implant, as shown in FIG. 4. This implant is the same size and construction as implants placed into hundreds of thousands of patients each year. A custom sensor unit was designed that was capable of fitting in the stem extender of the tibial component of the knee implant. Four piezoresistive load cells 90a, 90b, 90c, 90d (NK Biotech, Minneapolis, Minn.) were located underneath tibial tray 92. Each was capable of measuring up to 200 pounds. Sensor unit 20' was mounted with remote powering coil 84b, as shown in FIG. 4.

The telemetry system and the remote powering coil were placed in the stem extender of the implant, as shown in FIG. 4. Radio antenna 33 is then sealed within hermetically sealed feedthrough 94 to allow for high frequency transmission to be transmitted out of housing 60'. Polyethelene cap 96 is then added to protect antenna 33 from damage during the implantation process. Load cells 90a, 90b, 90c, 90d in tibial tray 92 are then attached to sense unit 20' and tibial tray housing 60' is hermetically sealed to tibial tray 92 and hermetic feedthrough 94 using electron beam welding.

To determine bit error rate, the inventors performed long term (2 days) monitoring of checksum errors with the transmitter at 15 feet from the receiver with direct line of sight between the transmitter and receiver antennas. The bit error rate was measured at 10 ppm.

To test thermal stability, the inventors conducted temperature drift tests of one transmitter within our environmental chamber (Thermatron) from 15 to 50 deg. Celsius. Bridge completion (for the strain gauge inputs) was provided outside the chamber using precision resistors. Temperature stability was determined to be 10 ppm/° C. for offsets, and 100 ppm/° C. for gains.

The telemetry system was tested with a wide variety of different sensors to verify compatibility. The fact that the gain and digital filtering are programmable allows for a number of different sensors to be used with the sensor unit system. FIG. 5 lists sensors that were tested or have been verified to be compatible with the sensor unit system. Two different versions of sensor units were designed, one that is compatible with DC sensors (resistance, of voltage output sensors) and one that is compatible with sensors that require low power AC excitation (inductive and capacitive sensors).

From FIG. 5 it is apparent that a wide variety of physical parameters may be measured. For orthopedic implants, force transducers based on foil or piezoresistive semiconductor gauges are commonly employed for load measurements. Inductive displacement transducers could be employed for measurement of micro-motion of bone relative to an implant.

In a paper by D. D'Lima, J. Slamin, B. Morris, "An implantable telemetry system to measure intra-articular tibial forces", Orthopedic Research Society, Anaheim, Calif. 1999, the following results for the sensor unit, control unit, and power transfer scheme described herein above described here was described. The total knee implant application, tests demonstrated that the implant could transmit through bone, cement and soft tissue for 3 to 5 meters. Results comparing the magnitude of applied force to measured force show close agreement with a mean error of 1.2% up to loads of 2000 N. When the location along the x axis was considered, the mean error between the applied load location and the measured load location was <1 mm for the 6 different locations tested. For location along the y axis, the mean error between applied and measured location was 0.4 mm for the 6 different locations tested. When tibiofemoral axial compressive forces measured by the transducer were compared with those calculated from knee moments in the 2-D model, the mean error was <5% over 9 different combinations of flexion angles and loads (4).

Thus, a versatile remotely powered transmitter that can be applied to a number of different orthopedic applications has been developed. It was shown that it is feasible to inductively couple enough power through a titanium orthopedic implant to power the sensors and electronics. The system was verified to work with a number of sensors and testing of the system in vitro in a total knee implant has been successful. Direct in vivo load measurement will provide extremely valuable information for improvement of implant designs and may aid in the rapid rehabilitation of individuals in which devices have been implanted.

Sensor units mounted in wearable braces or on structures, such as bridges, buildings, or aircraft frames, can be used as well as with implants mounted within live subjects. All such sensor units can include datalogging, wireless data communications, and various sensors.

Datalogging allows for very fast data collection, but previous designs require a direct (hard wired) connection to a host computer in order to allow the data to be downloaded to the host computer for short term viewing and for long term analysis. The present inventors developed a bi-directional RF communications link to trigger a sample to be logged, as well as to request data to be transmitted to the host computer.

The present inventors designed and built a complete system for fast data collection and wireless data communications from an implanted or worn sensor array to a remote data acquisition system (DAS) hosted by a personal computer.

A small digital data transceiver, datalogger, analog signal conditioner, and triaxial accelerometer package (approximately the size of two dominoes) is affixed to various limb segments for linear and angular position/acceleration measurement. They may also be mounted to structures for measuring displacements and vibrations.

The subject wearing the brace with the sense unit is allowed to perform the activity to be monitored (skiing, boxing, football, tennis, etc.).

Control unit antenna 52 is placed within 95 feet of the subject, and control unit 50 can trigger microprocessor 26 to begin logging data to non-volatile memory 28 by sending a "request to begin sampling" byte to sense unit 20.

The duration of logging, or data sample duration, is factory programmed from 5 to 20 seconds typical. For three channels of 16 bit data, 5 seconds uses approx. 0.5 megabits of data.

The subject or structure under test is brought within range (10-15 feet) of the host transceiver, and the host sends a "request to download data" byte from the remote (foot mounted) transceiver. At 9600 bits per second (baud) rate, data download is complete in approximately one minute.

To collect more data on additional runs with the same subject, the control unit sends a "request to begin sampling" byte again. Depending on how much memory is available, the sense unit may add to or overwrite data saved in remote datalogger's memory 28 with data from the new run.

Control unit 50 can also transmit timing and address information to activate all sensor units or to activate specific sensor units based on the address of the individual sensor unit. While the processor may keep track of time, it is advantageous for control unit 50 to periodically transmit a time synching signal to one or more sensor units that resets a clock on microprocessor 26 in sensor unit 20 to a known time reference. This is especially advantageous when trying to synchronize to another sensor device, such as a video camera, which could require millisecond level time resolution and could be synchronized by the timing signal from control unit 50. Control unit 50 uses software capable of saving and displaying data downloaded from sense unit 20.

Most efficient use of non-volatile memory 28 can be tailored in software for specific applications. For example, slowly changing data (such as temperature) can be sampled infrequently. Conversely, very fast events could be sampled when triggered by an event (or by the external transceiver) for short time periods. Data could be downloaded on request from the external transceiver 54, as required by the application. To prevent accidental loss, microprocessor 26 can ensure that no data in memory 28 is overwritten unless data is successfully downloaded to control unit 50 first.

The present invention is also applicable to sensing chemical reactions such as curing of composite materials. One or more sensor units 20 can be embedded within a composite structure, remotely powered, and interrogated by personal computer 56 through a non-contacting inductive link, such as coils 84a, 84b.

The present inventors enhanced sensor unit function by developing specialized sensor units for use with accelerometers, inclinometers, strain gauge rosettes, inductive transducers, and capacitive sensors. Sensor unit packaging has been subjected to environmental testing to insure robustness, and suitability for use in the target composite material.

A system was developed that was shown to transfer 15 mA through radio absorptive graphite composite 10 mm thick, using 25 watts of excitation power. This excitation signal also carried interrogation command data encoded by shifting the frequency of the power carrier.

It has been noted that the viability of such a system for cure temperature monitoring in composite panel fabrication processes would be dramatically improved if the gap between the excitation coil and the embedded sensor network could be increased to 150 mm.

It is technically difficult to achieve full power operation (continuously sampling, powering, and transmitting data at the maximum data rate) of the embedded sensor unit with 150 mm gap. Assuming a constant power applied to the excitation coil, the power induced in the receiving coil drops inversely proportional to the cube of the distance from the excitation coil. This means if the distance is doubled to 20 mm, the available power is reduced by a factor of 8. As the distance is increased ten times (to 100 mm) the available power is now reduced by a factor of 1000. The 150 mm represents a 15 times increase in distance over the originally specified 10 mm gap between excitation and receive coils. This theoretically requires an increase in excitation power or a reduction in embedded system power requirements, this reduction in power requirement can be achieved by data logging rather than by continuous RF data transmission. The data is then retrieved when it is possible to either increase power or reduce the distance between excitation and receiving coils 84a, 84b. The present inventors have found that the current draw of the embedded sensor unit will be reduced to less than 100 uA by datalogging.

As previously discussed, a barrier to powering these devices from a longer range is the requisite supply current of the embedded system. Currently, the largest power requirement of the embedded system is the data transmission system that is required to receive data from the host and transmit data from the structure. If the power requirements were reduced, than the distance between the powering coil and the embedded receiving coil could be increased. It is acceptable to collect data during the temperature curing process and save the data internally for transmission at a later time after the cure is complete. After the cure is complete, it is also acceptable to allow closer coupling between the external and embedded coils, which allows for data to be transmitted out of the composite.

The sensor units power down the transmitters and receivers during data collection, saving significant power supply current. In addition, if the bandwidth required of the sensor measurements is low, the power could be reduced even more through the use of sensor power multiplexing and reduction in microprocessor clock frequency. Sensor multiplexing means that power is applied to the sensors only when being sampled, which reduces the average power over time required by the sensors. Reducing the frequency of the processor clock will also lower the power required by the system due to a reduction in CMOS switching losses. For example, by reducing the clock frequency by a factor of four and utilizing datalogging as opposed to constantly transmitting data, the power can be reduced by an order of magnitude. In the case of temperature sensing, we would be able to reduce the power by two orders of magnitude, due to low current consumption and low data bandwidth required by these sensors.

The downloading of the data is managed by modulation of the level of the power to the embedded system. When the coupled power is great enough, then this will indicate to the embedded node to place the sensor unit in download data mode to download the logged data. Along with the logged data, a confirmation byte that a complete data set has been stored is transmitted to the control unit. As long as the power level is maintained above a certain threshold, the embedded node will continuously retransmit the contents of the logged data memory. This will ensure that data will be received in its entirety. When the power coupled is low, the system reverts to low power data collection mode. In this manner, the external system has full control of the mode of the embedded sensor unit by controlling the transmitted power level.

While several embodiments of the invention, together with modifications thereof, have been described in detail herein and illustrated in the accompanying drawings, it will be evident that various further modifications are possible without departing from the scope of the invention. Nothing in the above specification is intended to limit the invention more narrowly than the appended claims. The examples given are intended only to be illustrative rather than exclusive.

What is claimed is:

1. A data collection apparatus, comprising:
a sensing unit for sensing a parameter comprising a sensor, a first data storage device, a first receiving device, and a first transmitting device, said first data storage device for storing data from said sensor, said first transmitting device for transmitting data derived from said sensor;
a control unit separate from said sensing unit, said control unit comprising a second receiving device, a second transmitting device, and a second data storage device different from said first data storage device, said second receiving device to receive data transmitted from said sensing unit, said second data storage device for storing said data received from said sensing unit wherein said sensing unit is configured so a real time signal triggers a change in at least one from the group consisting of: (a) sensor data handling, (b) sensor data collection, (c) sensor data storage in said sensing unit, and (d) sensor data transmission from said sensing unit, wherein all power for powering said sensing unit is derived from said control unit.

2. The apparatus as recited in claim 1, wherein said sensor comprises at least one from the group consisting of an accelerometer, a displacement sensor, a strain gauge, a pressure gauge, a thermometer, a flow monitor, a heart monitor, an electrocardiogram (EKG), an electromyogram (EMG), an electroencephalogram (EEG), a blood monitor, a force gauge, a humidity monitor, a growth rate monitor, a ripeness monitor, a light intensity gauge, a radiation detector, a chemical detector, a corrosion detector, and a toxic monitor.

3. The apparatus as recited in claim 2, wherein said sensor comprises an array of said accelerometers.

4. The apparatus as recited in claim 2, wherein said sensor comprises a linear accelerometer.

5. The apparatus as recited in claim 2, wherein said sensor comprises a resistive accelerometer.

6. The apparatus as recited in claim 2, wherein said sensor comprises an angular accelerometer.

7. The apparatus as recited in claim 2, wherein said sensor comprises a piezoelectric accelerometer.

8. The apparatus as recited in claim 1, wherein said sensor detects vibration.

9. The apparatus as recited in claim 1, wherein said sensing unit is attached to at least one from the group consisting of an architectural structure and a vehicle.

10. The apparatus as recited in claim 1, wherein said sensing unit is worn by a live subject.

11. The apparatus as recited in claim 1, wherein said sensing unit further comprises a microprocessor.

12. The apparatus as recited in claim 11, wherein said microprocessor is connected to said first storage device, said first transmitting device, and said first receiving device.

13. The apparatus as recited in claim 11, wherein said microprocessor comprises a triggering device for triggering said change.

14. The apparatus as recited in claim 11, wherein said microprocessor comprises a triggering device that initiates transmission of data from said sensing unit to said control unit, wherein said triggering device is controlled by a real time change in said data.

15. The apparatus as recited in claim 1, wherein said sensing unit further comprises a power supply.

16. The apparatus as recited in claim 15, wherein said power supply comprises a rechargeable battery.

17. The apparatus as recited in claim 16, further comprising a circuit for recharging said battery by inductive coupling.

18. The apparatus as recited in claim 17, further comprising a hermetically sealed housing, wherein said sensor and said circuit for recharging are in said housing and said coupling is through said housing.

19. The apparatus as recited in claim 17, wherein said circuit for recharging is in said housing and an antenna for said coupling is located outside said housing.

20. The apparatus as recited in claim 1, wherein said first receiving device comprises an RF receiver for receiving said real time signal.

21. The apparatus as recited in claim 1, wherein said first transmitting device includes an RF transmitter.

22. The apparatus as recited in claim 1, wherein said sensing unit includes a clock, wherein said control unit includes a time reference, and wherein said second transmitting device is configured to send a timing signal to said sensing unit for synchronizing said clock to said time reference.

23. The apparatus as recited in claim 22, wherein a plurality of sensing units include clocks, wherein said timing signal synchronizes said clocks on a plurality of said sensing units.

24. The apparatus as recited in claim 22, wherein said first storage device is connected to receive and record said timing signal.

25. The apparatus as recited in claim 22, wherein said timing signal synchronizes clocks on said sensing unit and on another apparatus.

26. The apparatus as recited in claim 1, wherein said first data storage device continually records.

27. The apparatus as recited in claim 1, wherein said sensing unit further includes a feedback device for adjusting said parameter based on said data.

28. The apparatus as recited in claim 27, further comprising a sensor for detecting excessive vibration, wherein said feedback device is an active damping element to reduce vibration in response to excessive vibration.

29. The apparatus as recited in claim 1, wherein said second data storage device comprises a computer.

30. The apparatus as recited in claim 1, wherein said control unit further comprises a device to signal a user that data exceeding a preset threshold has been reached.

31. The apparatus as recited in claim 1, further comprising a plurality of sensing units, wherein said second transmitting device is connected to transmit address information to said sensing units to activate at least one from the group consisting of all of said sensing units, specific ones of said sensing units, and an individual sensing unit of said plurality of sensing units.

32. The apparatus as recited in claim 1, further comprising a host computer, wherein said control unit is connected to said host computer.

33. The apparatus as recited in claim 32, wherein said host computer is configured to accept user input, wherein a user operating on said host computer sends a signal for triggering data collection.

34. The apparatus as recited in claim 33, further comprising a triggering device.

35. The apparatus as recited in claim 1, wherein said sensing unit is configured so data from said sensor triggers transmission from said sensing unit to said control unit.

36. The apparatus as recited in claim 35, wherein said sensing unit is configured to trigger transmission from said sensing unit to said control unit once sensor data exceeds a threshold value.

37. The apparatus as recited in claim 1, wherein said first data storage device is controlled by data received by said sensor.

38. The apparatus as recited in claim 37, wherein when said data received by said sensor reaches a threshold, data in said first storage device is retained.

39. The apparatus as recited in claim 38, wherein said retained data includes data received after said data received by said sensor reaches said threshold.

40. The apparatus as recited in claim 1, wherein said sensing unit is configured to be triggered by at least one from the group consisting of a real time change in information that exceeds a predetermined threshold, a change in information about a structure or subject being monitored, detection of inactivity for a period of time exceeding a predetermined time, receiving a signal from an analyst, an event sensed by said sensor, and receiving a real time signal from said control unit to said sensing unit.

41. The apparatus as recited in claim 1, wherein said control unit comprises a first part and a second part, wherein said first part includes said second receiving device, said second transmitting device, and said second data storage device, wherein said second part includes a power amplifier, a signal generator and a transmitter coil, wherein said second part is separate from said first part, wherein all power for powering said sensing unit is derived from said second part.

42. The apparatus as recited in claim 1, further comprising a hermetically sealed housing, wherein said sensing unit is located in said hermetically sealed housing.

43. The apparatus as recited in claim 42 wherein said housing comprises at least one from the group consisting of titanium and ceramic.

44. The apparatus as recited in claim 42, wherein said sensing unit further comprises an antenna, wherein said antenna extends outside said housing and is connected within said housing through a penetration in said housing.

45. A method of collecting data, comprising:
  a) providing a sensing unit for sensing a parameter said sensing unit comprising a sensor, a first data storage device, a first receiving device, and a first transmitting device, said first data storage device for storing data from said sensor, said first transmitting device for transmitting data derived from said sensor;
  b) providing a control unit separate from said sensing unit, said control unit comprising a second receiving device, a second transmitting device, and a second data storage device different from said first storage device, said second receiving device for receiving data transmitted from said sensing unit, said second data storage device for storing said data received from said sensing unit, wherein all power for powering said sensing unit is derived from said control unit;
  c) transmitting a real time signal from said control unit to said first receiving device to trigger a change in at least one from the group consisting of sensor data handling, sensor data collection, storage of sensor data in said first sensing unit, and transmission of data from said sensing unit;
  d) triggering transmitting data from said first sensing unit to said second receiving device.

46. The method as recited in claim 45, wherein said triggering transmitting data includes generating a trigger signal within said sensing unit.

47. A data collection apparatus, comprising a network of addressable sensing units and a separate control unit, wherein each addressable sensing unit of said network of addressable sensing units has an individual address, wherein said control unit includes a communications device for transmitting address information to communicate with an individual addressable sensing unit based on said individual address, wherein said sensing units each comprise a sensor, a microprocessor, a first data storage device connected to said microprocessor, a first transmitting device and a first receiving device, wherein said sensing units are configured so a real time signal from said control unit to at least one said sensing unit triggers a change in at least one from the group consisting of: (a) data handling, (b) data collection, and (c) data storage in said sensing unit, and (d) sensor data transmission from said sensing unit to said control unit, wherein all power for powering said sensing units is derived from said control unit.

48. The apparatus as recited in claim 47, wherein said control unit comprises a second transmitter, a second receiver, and a second data storage device for storing data received from said sensing units.

49. The apparatus as recited in claim 48, wherein said second transmitter is connected to transmit address information to activate at least one from the group consisting of all of said sensing units, specific ones of said sensing units, and one of said sensing units.

50. The apparatus as recited in claim 48, wherein said control unit is configured to provide an address to query each sensing unit individually.

51. The apparatus as recited in claim 48, wherein said second transmitting device transmits a timing signal for synchronizing said plurality of sensing units.

52. The apparatus as recited in claim 47, wherein said microprocessor is programmed to do at least one from the group consisting of: (a) query, (b) activate, and (c) send timing information to each sensing unit individually, and (d) activate all sensing units at once.

53. The apparatus as recited in claim 47, wherein said sensing units further comprise a signal conditioner, an analog to digital (A/D) converter, and a clock for microprocessor functions and to track time.

54. The apparatus as recited in claim 47, wherein said first data storage device is connected to said first transmitting device for transmitting data to said control unit when a real time signal triggering transmission is received.

55. The apparatus as recited in claim 47, wherein said first transmitter and said second transmitter are wireless transmitters.

56. The apparatus as recited in claim 47, wherein each said sensing unit further comprises a triggering device.

57. The apparatus as recited in claim 47, wherein each said sensing unit is configured so data from said sensor triggers transmission from said sensing unit to said control unit.

58. The apparatus as recited in claim 57, wherein each said sensing unit is configured to trigger transmission from said sensing unit to said control unit once sensor data exceeds a threshold value.

59. A data collection apparatus, comprising:
a plurality of sensing units for sensing a parameter, said sensing units each comprising a sensor, a first data storage device, a first transmitting device and a first receiving device;
a control unit separate from said sensing units, said control unit comprising a second transmitting device, a second receiving device, and a second data storage device, said second data storage device for storing data received from said sensing units, wherein each of said sensing units is configured so a real time signal from said control unit to said sensing unit is configured to trigger transmitting data derived from said sensor by said first transmitting device to said second receiving device; and
wherein each sensing unit of said plurality of sensing units has unique address, and wherein said control unit includes a communications device for transmitting address information to communicate with an individual sensing unit based on said unique address, wherein all power for powering said individual sensing unit is derived from said control unit.

60. The apparatus as recited in claim 59, wherein said second transmitting device is further transmits timing information to said sensing units.

61. The apparatus as recited in claim 59, wherein said address information activates at least one from the group consisting of all of said sensing units, specific ones of said sensing units, and one of said sensing units.

62. The apparatus as recited in claim 59, wherein said control unit is configured to provide an address to query each sensing unit individually.

63. The apparatus as recited in claim 59, wherein said sensing units each further comprise a plurality of sensors wherein said microprocessor is programmed to do at least one from the group consisting of (a) query each of said sensing units individually (b) activate each of said sensing units individually (c) query all said sensing units at once and (d) activate all said sensing units at once.

64. The apparatus as recited in claim 59, wherein said sensing units each further comprise a signal conditioner and an A/D converter.

65. The apparatus as recited in claim 59, wherein said microprocessor controls storage to said first data storage device.

66. The apparatus as recited in claim 59, wherein said first transmitting device is configured to transmit data from said first storage device to said control unit.

67. The apparatus as recited in claim 59, wherein said second receiving device and second data storage device are for receiving and storing said data transmitted to said control unit.

68. The apparatus as recited in claim 59, wherein said first transmitting device and said second transmitting device are wireless transmitters.

69. The apparatus as recited in claim 59, further comprising a triggering device.

70. The apparatus as recited in claim 59, wherein each said sensing unit is configured so data from said sensor triggers transmission from said sensing unit to said control unit.

71. The apparatus as recited in claim 70, wherein each said sensing unit is configured to trigger transmission from said sensing unit to said control unit once sensor data exceeds a threshold value.

72. A method of collecting data, comprising:
a) providing a sensing unit for sensing a parameter, said sensing unit comprising a sensor, a first data storage device, a first receiving device, and a first transmitting device, said first data storage device for storing data from said sensor, said first transmitting device for transmitting data derived from said sensor;
b) providing a control unit separate from said sensing unit, said control unit comprising a second receiving device, a second transmitting device, and a second data storage device different from said first storage device, said second receiving device for receiving data transmitted from said sensing unit, said second data storage device for storing said data received from said sensing unit, wherein all power for powering said sensing unit is derived from said control unit; and
c) transmitting a real time signal from said control unit to said first receiving device to trigger a change in at least one from the group consisting of sensor data handling, sensor data collection, sensor data storage in said first sensing unit, and data transmission from said sensing unit.

73. A method as recited in claim 72, wherein said sensing unit senses a parameter of a subject, wherein said subject includes at least one from the group consisting of an architectural structure and a vehicle.

* * * * *